US009566136B2

(12) United States Patent
Vercellotti et al.

(10) Patent No.: US 9,566,136 B2
(45) Date of Patent: Feb. 14, 2017

(54) ENDOSSEOUS DENTAL IMPLANT

(75) Inventors: Tomaso Vercellotti, Genoa (IT); Alberto Rebaudi, Genoa (IT)

(73) Assignee: REX IMPLANTS, LLC, Columbus, OH (US)

( * ) Notice: Subject to any disclaimer, the term of this patent is extended or adjusted under 35 U.S.C. 154(b) by 0 days.

(21) Appl. No.: 13/514,725

(22) PCT Filed: Dec. 6, 2010

(86) PCT No.: PCT/EP2010/069003
§ 371 (c)(1),
(2), (4) Date: Jun. 8, 2012

(87) PCT Pub. No.: WO2011/069978
PCT Pub. Date: Jun. 16, 2011

(65) Prior Publication Data
US 2012/0251977 A1  Oct. 4, 2012

(30) Foreign Application Priority Data

Dec. 11, 2009 (IT) .............................. GE2009A0097
May 20, 2010 (IT) .............................. GE2010A0056

(51) Int. Cl.
*A61C 13/00* (2006.01)
*A61C 8/00* (2006.01)
(52) U.S. Cl.
CPC ................... *A61C 8/0019* (2013.01)
(58) Field of Classification Search
CPC .............. A61C 8/0019–8/0021; A61C 8/0027; A61C 8/0037
USPC ....................... 433/172–176, 201.1
See application file for complete search history.

(56) References Cited

U.S. PATENT DOCUMENTS

| 3,729,825 A |   | 5/1973  | Linkow et al. |         |
|-------------|---|---------|---------------|---------|
| 3,905,109 A | * | 9/1975  | Cohen et al.  | 433/174 |
| 3,950,850 A |   | 4/1976  | Driskell et al.|         |
| 4,177,562 A | * | 12/1979 | Miller et al. | 433/174 |
| 4,573,922 A | * | 3/1986  | Bello         | 433/176 |
| 4,713,003 A | * | 12/1987 | Symington et al. | 433/173 |
| 4,762,492 A | * | 8/1988  | Nagai         | 433/174 |
| 4,799,886 A | * | 1/1989  | Wimmer        | 433/176 |

(Continued)

FOREIGN PATENT DOCUMENTS

DE          24 54414         5/1975

OTHER PUBLICATIONS

International Search Report for PCT/EP2010/069003 Dated Mar. 25, 2011.

(Continued)

*Primary Examiner* — Yogesh Patel
(74) *Attorney, Agent, or Firm* — Jason H. Foster; Kremblas & Foster

(57) ABSTRACT

Dental implant, having a central body (1) with a substantially conical or frustoconical shape and having, extending from the end with a larger cross-section, a connection seat (701) able to receive a stump pin; this central body (1) is provided with a blade (2) positioned in a longitudinal mid-plane of said central body (1) and has a length so as to protrude beyond the end of the central body (1) which has a smaller cross-section; the central body (1) and the blade (2) are able to give the implant a substantially wedge-like form able to epand the bone during insertion.

20 Claims, 4 Drawing Sheets

(56) References Cited

U.S. PATENT DOCUMENTS

| | | | |
|---|---|---|---|
| 4,997,383 A * | 3/1991 | Weiss et al. | 433/176 |
| 5,102,336 A | 4/1992 | Linkow | |
| 5,116,226 A * | 5/1992 | Linkow | 433/176 |
| 6,921,264 B2 * | 7/2005 | Mayer et al. | 433/173 |
| 7,303,396 B2 * | 12/2007 | Abarno | 433/173 |
| 2003/0087217 A1 * | 5/2003 | Coatoam | 433/173 |
| 2004/0038180 A1 | 2/2004 | Mayer et al. | |
| 2004/0053196 A1 | 3/2004 | Mayer et al. | |
| 2006/0216673 A1 * | 9/2006 | Park | 433/173 |
| 2006/0292526 A1 * | 12/2006 | Simmons | 433/201.1 |
| 2009/0061389 A1 * | 3/2009 | Lomicka et al. | 433/201.1 |

OTHER PUBLICATIONS

Written Opinion of the International Searching Authority for PCT/EP2010/069003 Dated Mar. 25, 2011.

* cited by examiner

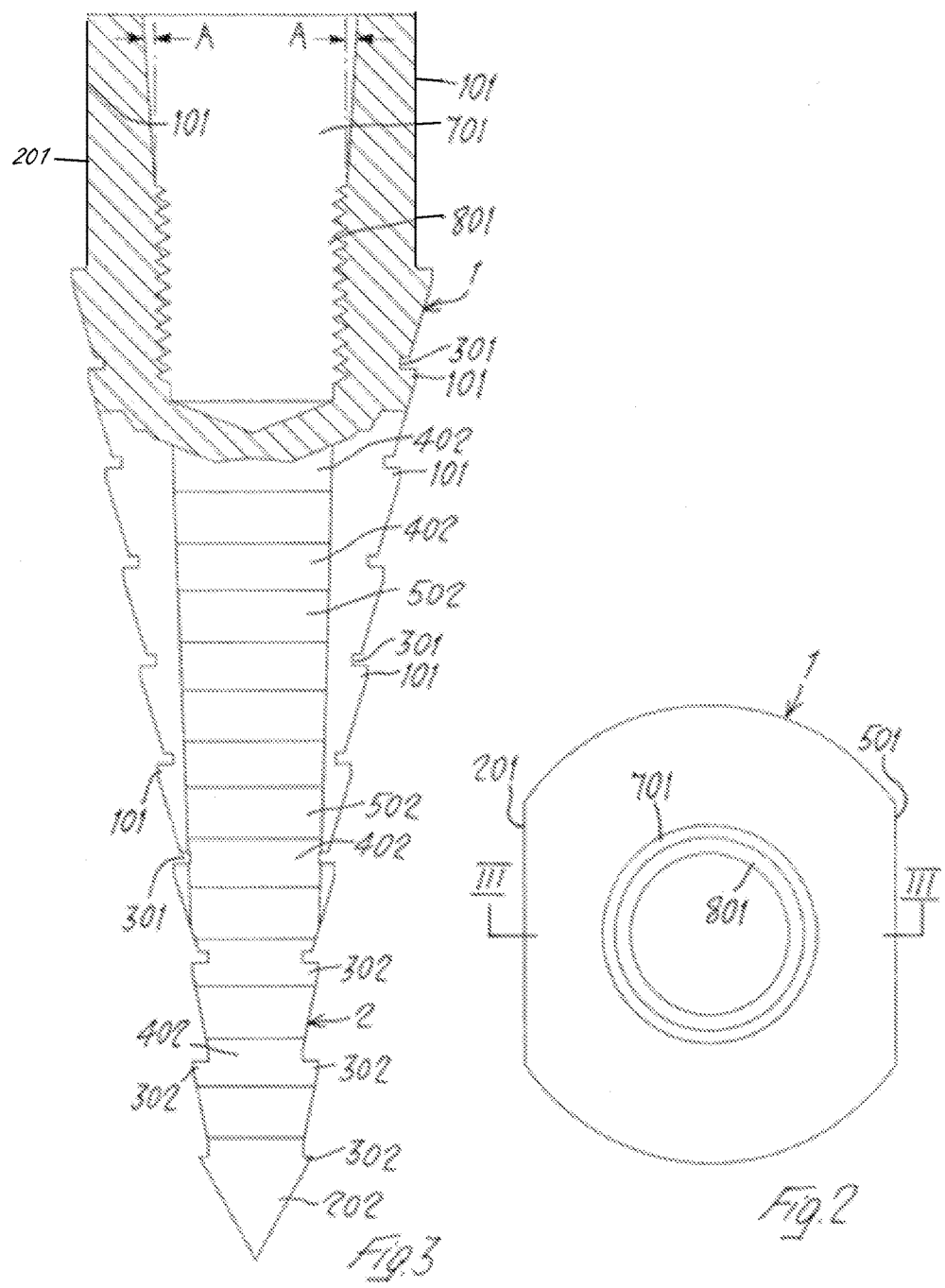

ENDOSSEOUS DENTAL IMPLANT

The present invention relates to dental implants.

BACKGROUND OF THE INVENTION

As is known, when performing dental implants, pins are fixed onto the jaw or onto the upper jaw bone of the patient in predetermined positions. These implants are also provided at the top with a seat inside which stump pins or the like are fixed. There are cases where the thickness of the patient's bone in which the implant is to be performed is very small, for example from 2.5 mm to 6 mm, and in such cases insertion of the implant is very difficult since, in order to be able to insert the implant, it is required to perform complicated regenerative surgery using special bone grafts. Usually, a normal implant, which has a main body with a cylindrical cross-section, requires a thickness of the bone crest at least 2 mm greater than its diameter.

The object of the present invention is therefore to provide a dental implant which may be advantageously applied even in small-thickness zones of the bone crest of the patient, has limited volumetric dimensions, provides optimum anchoring in the bone, has a surface area similar to that of standard-size implants and ensures an excellent primary stability.

SUMMARY OF THE INVENTION

This object is achieved by the present invention by means of a dental implant, characterized in that it comprises a central body with a substantially conical or frustoconical shape and having, extending from the end with a larger cross-section, a connection seat able to receive a stump pin; this central body is provided with a blade positioned in a longitudinal mid-plane of said central body and having a length such as to protrude beyond the end of said central body which has a smaller cross-section; said central body, which is extremely thin also in the coronal part, and said blade are able to give the implant a substantially wedge-like form.

According to a further aspect of the present invention the present dental implant comprises at least on the front or rear surface of said central body and said blade at least one longitudinal guide rib projecting from said surface.

According to yet another aspect of the present invention said central body and said blade have an angle of conicity of about 1° or less so as to give the implant a substantially blade-like form.

The presence of the longitudinal rib and the substantially blade-like form of the present implant allow the latter to be inserted more easily and more precisely inside the patient's bone since this insertion step is performed along a predetermined insertion axis which is always maintained, without undesirable transverse displacements. The implant thus has an even greater primary stability, allowing perfect anchoring which prevents possible transverse movements. The substantially blade-like form ensures, moreover, even more efficient and simple insertion of said implant in bone zones with a small bone volume or in zones with atrophic crests. This rapid and simple insertion of the present implant decreases advantageously the surgery time, reducing therefore the risk of infection and bone trauma. Differently from the preceding implants with a blade-like form, this implant has the function of expanding the bone during insertion and has a width and volume which lie within the normal dimensions of a standard implant and each of these implants may therefore replace a single tooth.

BRIEF DESCRIPTION OF THE DRAWINGS

Further objects and advantages of the present invention will be understood more clearly during the course of the following description which is provided by way of a non-limiting example with reference to the accompanying drawings in which:

FIG. 2 shows a top plan view of the dental implant according to FIG. 1;

FIG. 3 shows a cross-sectional view along the line III-III of FIG. 2;

DETAILED DESCRIPTION OF THE PREFERRED EMBODIMENTS

Figure 1:
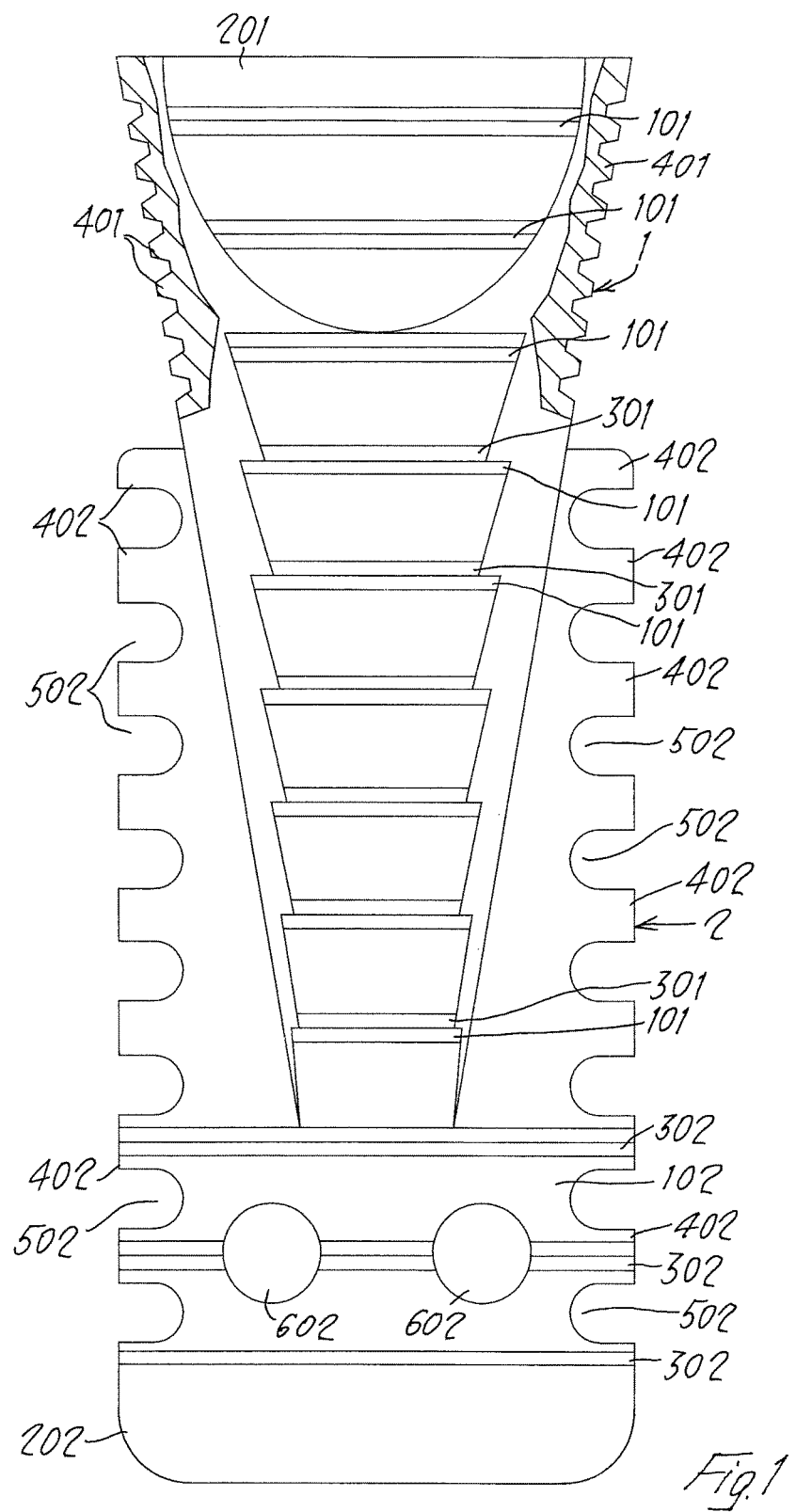
FIG. 1 shows a front view of a first embodiment of a dental implant according to the present invention.

With reference to the accompanying drawings and with particular reference to FIG. 1 thereof, 1 denotes the central body, with a substantially conical or frustoconical shape, of the present dental implant according to a first embodiment of the invention, while 2 denotes a rectangular or square blade which is formed as from a certain height of the central body 1 and is positioned along a longitudinal mid-plane of said central body. This blade 2 comprises an end part 102 which extends at the bottom beyond the end of the central body 1 with a smaller cross-section and is provided at the end with a transverse tip 202 which has edges which are suitably chamfered in order to avoid undesirable damage to the patient's bone. Said rectangular blade 2 and said central body 1 thus give the present implant a substantially wedge-like form. A series of transverse teeth 101 located on two diametrically opposite surfaces of said central body 1—in this case on the front surface and on the rear surface thereof—are formed along the entire surface of the central body 1 (see also FIG. 3 of the accompanying drawings). Transverse grooves 301 of suitable size are formed between each pair of adjacent front and rear transverse teeth 101: the grooves with a greater depth ensure a high primary stability, reducing the lateral and vertical micro-movements of the implant, while the grooves with a smaller depth ensure a high secondary stability, increasing the surface area of the implant. The top part of the central body 1 with a larger cross-section is provided with two diametrically opposite flattened surfaces substantially in the form of an arc of an ellipse, namely (see also FIG. 2 of the accompanying drawings) the front flattened surface 201 and the rear flattened surface 501. The transverse teeth 101 are also formed in these flattened surfaces 201 and 501 and extend so as to be bounded by these flattened surfaces 201 and 501. A thread 401 comprising a plurality of small teeth is formed in the top part of the central body 1, corresponding to the neck of the endosseous part. Transverse teeth 302 which extend over the entire width of this blade are also formed on the front and rear surfaces of the end part 102 of the blade 2. The latter series of teeth 302 formed in the vicinity of the tip 202 of the blade 2 may also not be provided. A series of teeth 402 separated by suitable grooves 502 with a substantially semicircular shape are formed along the entire length of each of the longitudinal edges of the blade 2. These longitudinal edges of the blade 2 provided with teeth 402 are positioned symmetrically with respect to the central body 1. The end part 102 of the blade also has, formed therein, one or more through-holes 602, for example two through-holes, designed to allow, once the implant has been inserted into the patient's bone, more rapid vascularization and also optimum grip and integration within the bone.

The top end of the central body 1 with a larger cross-section has, formed therein, a connection seat 701 with a small angle A of conicity which may vary from about 1° to about 2° with respect to a generic cylindrical hole. A threaded cylindrical hole 801 is provided at the bottom of this connection seat 701: a stump pin for the present implant will be engaged inside this seat 701 and this threaded cylindrical hole 801. Owing to this small angle A of conicity a series of advantages may be obtained: the so-called cold welding together of the seat 701 of the implant and the stump pin which is to be inserted inside this seat, with a consequent and advantageous reduction in the internal space and therefore a reduction in the spaces which may favour the proliferation of bacteria: and a horizontal coronal zone which is useful as a zone for supporting the connecting tissues and bone.

The central body 1 and the blade 2 are preferably made of a titanium/aluminium/vanadium alloy, Ti—Al$_6$—V$_4$ (pure titanium or alloy of titanium, tantalum, zirconia, ceramic material, or using other materials which are biocompatible and/or suitable for bone grafts) and the site where the implant must be inserted is prepared preferably using a piezoelectric surgical technique and technology, i.e. "piezo-surgery", which is known per se, or using other technologies such as sonic technology, laser technology or manual instruments such as blades or osteotomes. The front and rear teeth 101 and 302 project from the surface of the conical body 1 and the blade 2 in the manner of saw teeth, namely are provided with inclined surfaces able to facilitate insertion of the implant in the patient's bone and, in combination with the grooves 301, ensure optimum anchoring and stability once the implant has been inserted in the patient's bone. These teeth may have different forms depending on different constructional versions.

According to the embodiment of the invention described above, the implant formed by the central body 1 and the blade 2 and having a substantially wedge-like shape may advantageously be fixed also in zones where the patient's bone has a small thickness; this wedge-like form allows expansion of both the cortical and the spongy bone, taking advantage of its viscoelastic properties. Therefore, the vestibular cortical bone may also expand with respect to the lingual/palatine bone after performing on the patient's bone a thin osteotomy or a cut, providing a thin site inside which this implant is introduced. From a biological point of view the difference between the conventional implants and the present implant is notable since, in conventional implants, it is required to remove from the bone crest all the volume necessary for insertion of the implant using suitable milling cutters; in the present implant only a thin cut, which may vary for example from 0.1 mm to 1 mm, is required, therefore maintaining a sufficient thickness of the vestibular and palatal bone walls even in the presence of thin bone crests.

Figure 4:
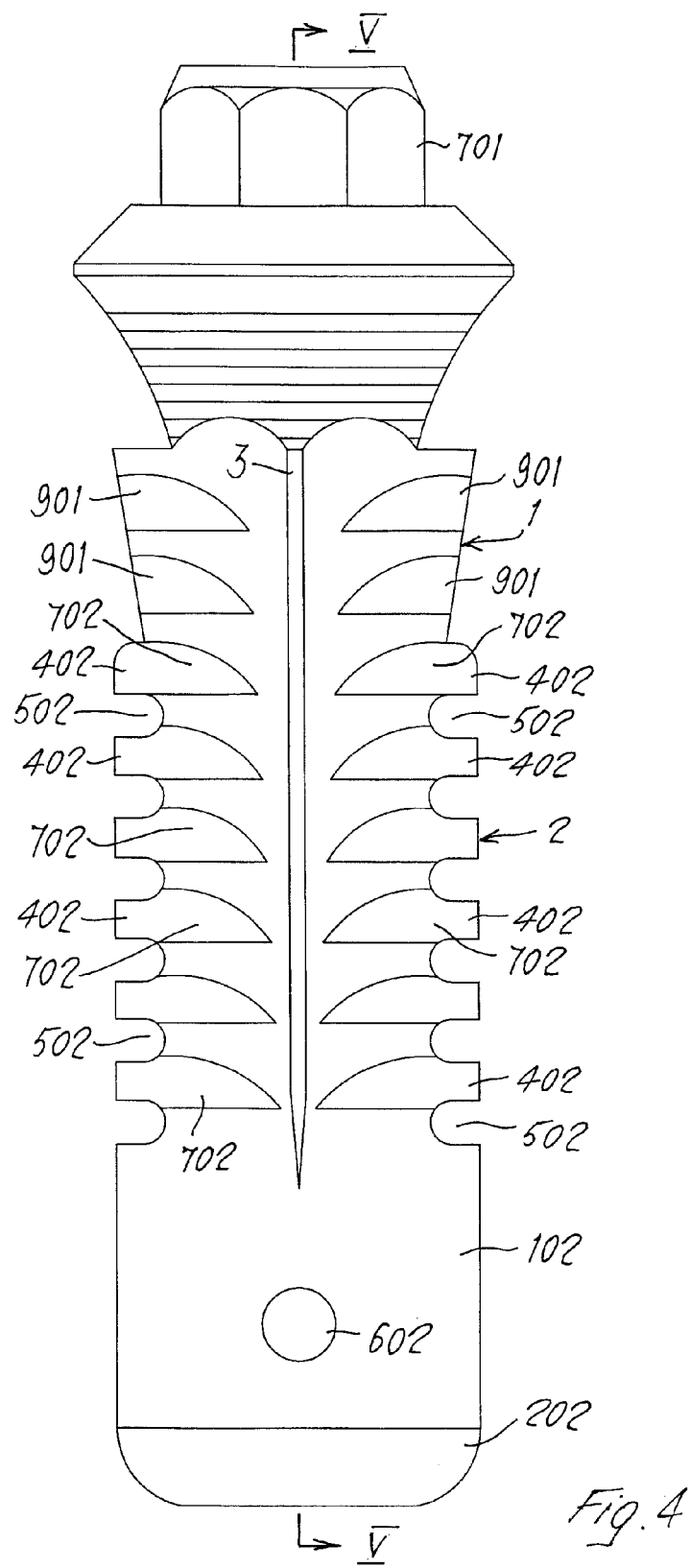
FIG. 4 shows a front view of a second embodiment of the dental implant according to the present invention.
Figure 5:
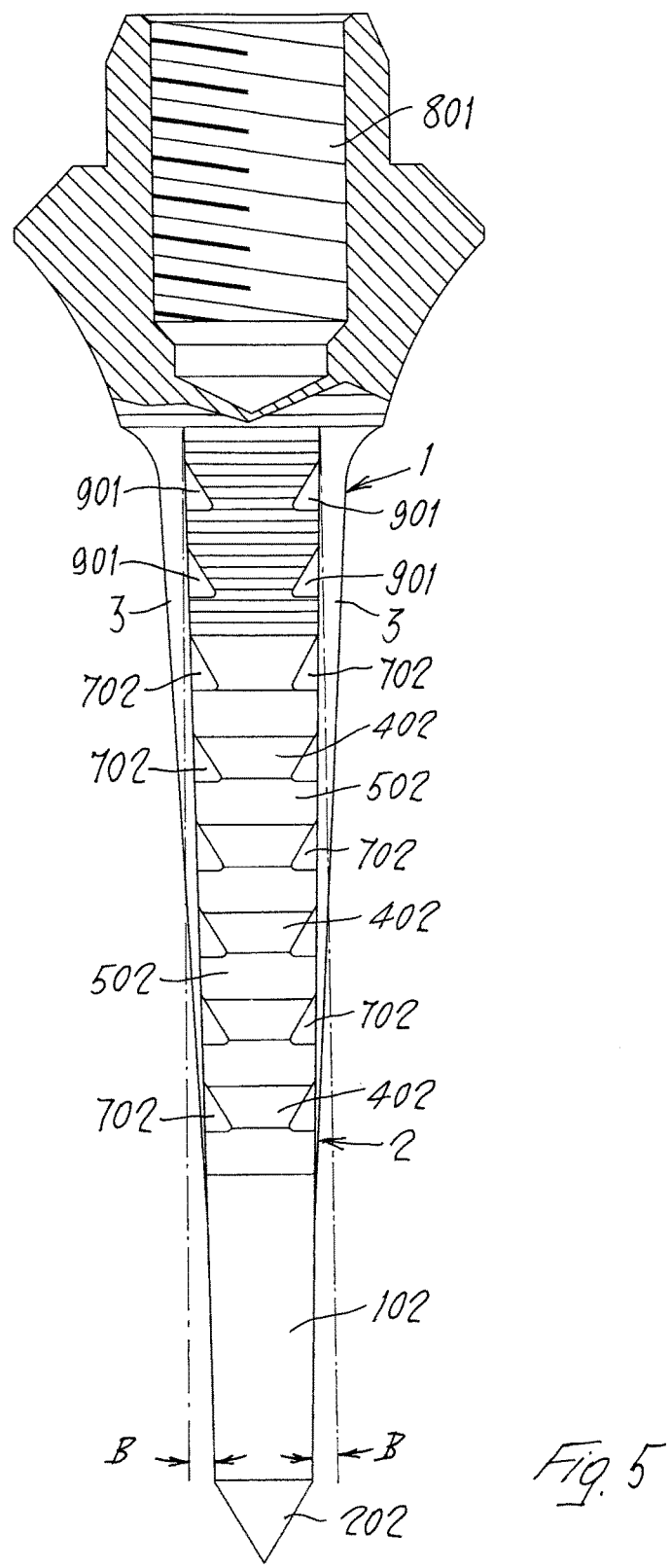
FIG. 5 shows a cross-sectional view along the line V-V of FIG. 4.

Suitably shaped recesses 901 which improve further the stability of the implant are formed along the front and rear surface of the central body 1—see FIGS. 4 and 5 in which identical parts are indicated by the same numbers used for the previous description. This central body 1 also comprises at the top the connection seat 701 comprising the threaded hole 801 for insertion of a stump pin for the present implant. In this embodiment also a series of teeth 402 separated by suitable grooves 502 with a substantially semicircular shape are formed along the whole length of each of the longitudinal edges of the blade 2. These longitudinal edges of the blade 2 provided with teeth 402 are positioned symmetrically with respect to the central body 1. A series of suitably shaped recesses 702 are formed on the front surface and on the rear surface of the blade 2, opposite said teeth 402 or said grooves 502. The end part 102 of the blade is also provided with a single through-hole 602 designed to allow, as mentioned above and once the implant has been inserted in the patient's bone, a more rapid vascularization and also optimum grip and integration within the bone.

A projecting longitudinal rib 3 designed to guide correctly the implant during its insertion inside the patient's bone is formed on each of the front and rear surfaces of said central body 1 and said blade 2, preferably in a central position. Each of these longitudinal ribs 3 helps facilitate insertion of the implant in the bone in such a way as to avoid damage to the bone itself and maintain constantly the predefined axis for insertion of the implant. These ribs 3 moreover increase the primary stability of the implant, allowing perfect anchoring which prevents possible transverse movements.

Preferably these longitudinal ribs 3 are identical and positioned so as to be diametrically opposite with respect to the main body 1 and to the blade 2, but in other embodiments they may also be single or asymmetric depending on the anatomical or biomechanical requirements. Each of these ribs 3 has a top end with a greater thickness in the top part of implant and a bottom end for connection to the blade 2. The thickness of the rib 3 therefore decreases from this top end towards this bottom end where the rib 3 is connected to the blade 2. According to other embodiments, these ribs may have thicknesses, forms and dimensions which are variable, continuous or with a sawtooth shape, in various constructional forms which are adapted to the anatomical variations of the available bone both with regard to height and thickness and in terms of density and quality.

The central body 1 and the blade 2 are designed so as to give the present implant a substantially blade-like form; in fact the angle of conicity B of the implant is in the region of 1° or less.

The blade-like form of this second embodiment of the present implant, which is therefore advantageously designed with a small thickness, allows the same to be used in a simple and efficient manner in bone zones with a very small bone volume or in zones with atrophic crests. The simplicity with which the present implant can be inserted also reduces advantageously the surgery time for installation of the implant, the possibility of infections and any undesirable damage to the bone.

The present implant is advantageously compatible with the stump pins of the most well-known implant manufacturers in the sector (31, SwissPlus, Branemark, Straumann, Zimmer) owing to an intermediate connection (between implant and stump) which may, in some cases, be separate from the implant and therefore be able to be added thereto during stages following that of implant insertion and, in other cases, may even already form part of the implant itself (thus forming a single piece), thereby creating a complete assembly which can already be combined with the other implant systems without further adaptation. This implant is also provided with an aesthetic finish on the neck and in the part emerging from the gums.

Moreover, despite the fact that the present implant has dimensional characteristics such that it may be inserted in thin crests, it has an excellent strength and standard-size surface area (bone contact area) and prosthetic connection, unlike the known implants where, following a reduction in the dimensions and in particular the diameter, both the bone contact area and the strength and dimensions of the prosthetic connection are reduced.

The invention claimed is:

1. Dental implant, comprising:
   a central body with a conical or frustoconical shape and having, extending from a top part of the central body, a connection seat able to receive a stump pin, wherein a top part of the central body has two diametrically opposite flat surfaces, and a plurality of teeth on the central body separated by grooves; and,
   a blade integrally formed with the central body and positioned in a longitudinal mid-plane of said central body and protruding beyond the sides and end of said central body, wherein the blade has a smaller cross-section than the central body, said central body and said blade are configured to give the implant a substantially wedge-like form having the function of expanding the bone during insertion, wherein the blade has, along longitudinal edges, a plurality of teeth separated by grooves, wherein the central body teeth are substantially smaller than the blade teeth.

2. Dental implant according to claim 1, wherein the longitudinal edges of the blade are positioned symmetrically with respect to said central body.

3. Dental implant according to claim 1, wherein said blade comprises a transverse end tip.

4. Dental implant according to claim 1, wherein said blade has a rectangular shape.

5. Dental implant according to claim 1, wherein at least two diametrically opposite walls of said central body are provided with a series of transverse teeth between which suitable grooves are formed.

6. Dental implant according to claim 5, wherein:
   said blade has a rectangular shape and has, along its longitudinal edges, a series of teeth which are separated by suitable grooves; and
   said tooth and said transverse teeth formed on two diametrically opposite walls of the central body and of the blade have an inclined surface so as to facilitate insertion of the implant in the patient's bone and at the same time be anchored to the patient's bone once the implant has been inserted.

7. Dental implant according to claim 1, wherein the blade has diametrically opposite walls, and transverse teeth are formed at least on said diametrically opposite walls.

8. Dental implant according to claim 1, wherein said blade comprises an end part in which one or more through-holes are formed.

9. Dental implant according to claim 1, wherein a threaded cylindrical hole is provided at the bottom of said connection seat and therefore towards the inside of the central body.

10. Dental implant according to claim 1, wherein said connection seat has a certain angle of conicity with respect to a generic cylindrical form.

11. Dental implant according to claim 1, wherein the top part of the central body is provided with a thread comprising a series of small teeth.

12. Dental implant according to claim 1, wherein said central body and said blade are made by using a titanium alloy, aluminium alloy, vanadium alloy or other materials which are biocompatible or suitable for bone grafts.

13. Dental implant according to claim 1, wherein the implant comprises, at least on the front or rear surface of said central body and said blade, at least one longitudinal guide rib projecting from said surface.

14. Dental implant according to claim 1, wherein said central body and said blade have an angle of conicity of about 1° or less so as to give the implant a substantially blade-like form.

15. Dental implant according to claim 1, wherein the implant comprises two ribs positioned on the front and rear surfaces of said central part and said blade so as to be diametrically opposite each other.

16. Dental implant according to claim 1, wherein a longitudinal rib is positioned centrally in said front or rear surface of said central part and said blade.

17. Dental implant according to claim 16, wherein said rib has a top end with a greater thickness in the top part of the implant and a bottom end for connection to the blade, the thickness of said rib decreasing from said top end towards said bottom end where the rib is connected to the blade.

18. Dental implant according to claim 1, wherein suitably shaped recesses are formed in said central part and/or in said blade.

19. Dental implant according to claim 1 which in a part emerging from the gums and the bone has a white, yellow or pink colored aesthetic finish or coating so as to blend in better with the color of the gums or the tooth.

20. Dental implant according to claim 1, including transverse teeth formed in said flat surfaces.

* * * * *